(12) United States Patent
Kovacs

(10) Patent No.: US 11,717,280 B2
(45) Date of Patent: Aug. 8, 2023

(54) MODULAR DISTRACTOR APPARATUS, SYSTEM, AND METHOD

(71) Applicant: INNOVATIVE MEDICAL PRODUCTS, INC., Plainville, CT (US)

(72) Inventor: Tamas Kovacs, Burlington, CT (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 204 days.

(21) Appl. No.: 17/364,689

(22) Filed: Jun. 30, 2021

(65) Prior Publication Data

US 2023/0000478 A1 Jan. 5, 2023

(51) Int. Cl.
*A61B 17/02* (2006.01)
*A61G 13/12* (2006.01)

(52) U.S. Cl.
CPC .... *A61B 17/025* (2013.01); *A61B 2017/0268* (2013.01); *A61B 2560/0443* (2013.01)

(58) Field of Classification Search
CPC .. A61G 13/12; A61G 13/1205; A61G 13/121; A61G 13/1215; A61G 13/122; A61G 13/1225; A61G 13/123; A61G 13/1235; A61G 13/124; A61G 13/1245; A61G 13/125; A61G 13/1255; A61B 17/025; A61B 2017/0268; A61B 2560/0443; A61B 90/57
See application file for complete search history.

(56) References Cited

U.S. PATENT DOCUMENTS

| | | | |
|---|---|---|---|
| 6,110,179 A * | 8/2000 | Flivik | A61B 17/8808 606/94 |
| D566,269 S | 4/2008 | Koros et al. | |
| 7,534,218 B2 | 5/2009 | Hiki | |
| D614,394 S | 4/2010 | Koshiishi | |
| 7,828,755 B2 | 11/2010 | Ikeuchi | |
| 8,007,456 B2 | 8/2011 | Stano | |
| D649,773 S | 12/2011 | Mahoney | |
| D649,774 S | 12/2011 | Mahoney | |
| D660,971 S | 5/2012 | Franke et al. | |
| 8,590,080 B1 | 11/2013 | Staresinic | |
| D714,376 S | 9/2014 | Chapman | |

(Continued)

FOREIGN PATENT DOCUMENTS

| | | |
|---|---|---|
| CN | 302012199 S | 7/2012 |
| EP | 2806837 B1 | 6/2017 |

(Continued)

*Primary Examiner* — Samuel S Hanna
(74) *Attorney, Agent, or Firm* — Nicholas E. Blanton, Esq.; Damian Wasserbauer, Esq.; Wasserbauer Law

(57) ABSTRACT

The present disclosure provides an apparatus, system, and method for positioning, holding, and/or distracting the bones and associated ligaments and tissue of the knee during surgery. In one aspect of the present disclosure, a modular distractor system may provide enhanced structurally stability and support of a patient's limb, which may provide stability, resulting in a better outcome for the patient. In another aspect of the present disclosure, modular distractor components are described, which provide for interchangeability and a tailored approach that accommodates variable patient limb size and specific surgical application.

1 Claim, 19 Drawing Sheets

(56) References Cited

U.S. PATENT DOCUMENTS

| | | |
|---|---|---|
| D716,459 S | 10/2014 | Liran et al. |
| 9,107,792 B2 | 8/2015 | Catacchio et al. |
| 9,339,430 B2 | 5/2016 | Jackson et al. |
| 9,480,616 B2 | 11/2016 | Kreuzer et al. |
| D775,353 S | 12/2016 | Anderson et al. |
| 10,159,620 B2 | 12/2018 | Sandler et al. |
| 10,376,287 B2 | 8/2019 | Torrie et al. |
| 10,518,404 B2 | 12/2019 | Barnes |
| 10,751,241 B2 | 8/2020 | Ferro et al. |
| 10,828,218 B2 | 11/2020 | Shandas et al. |
| 10,835,440 B2 | 11/2020 | Lane, II et al. |
| 10,874,539 B2 | 12/2020 | Lecursi et al. |
| 2002/0128577 A1 | 9/2002 | Smart |
| 2006/0225743 A1 | 10/2006 | Schuerch |
| 2008/0172791 A1 | 7/2008 | Walczyk |
| 2011/0201978 A1 | 8/2011 | Jeon et al. |
| 2016/0067137 A1 | 3/2016 | Little et al. |
| 2017/0196712 A1 | 7/2017 | Kazerooni et al. |

FOREIGN PATENT DOCUMENTS

| | | |
|---|---|---|
| JP | 5703037 B2 | 4/2015 |
| JP | 6261058 B2 | 1/2018 |
| KR | 1020160067819 A | 6/2016 |

\* cited by examiner

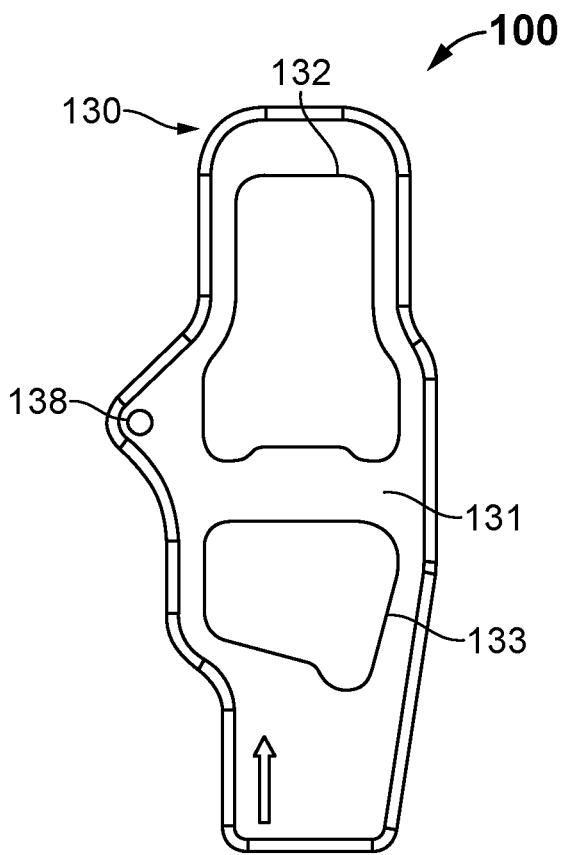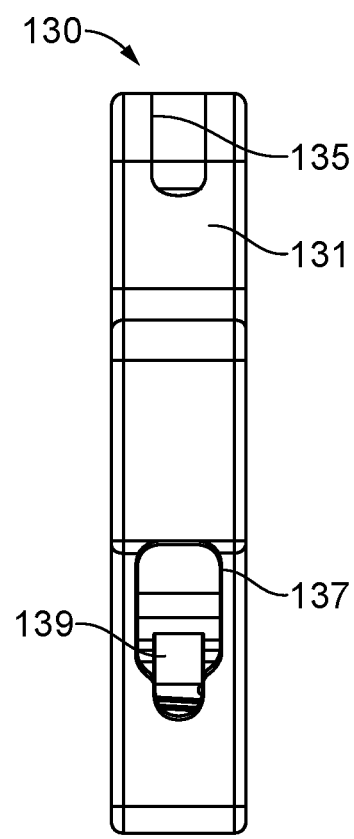
FIG. 15
FIG. 16
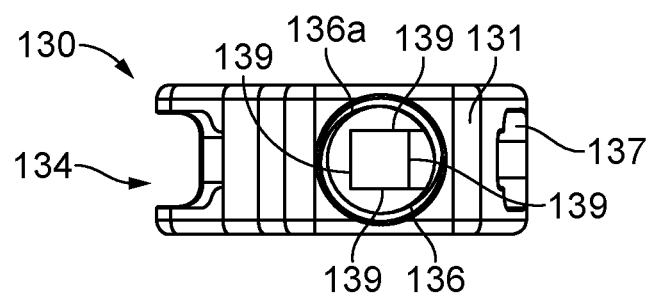
FIG. 17

MODULAR DISTRACTOR APPARATUS, SYSTEM, AND METHOD

TECHNICAL FIELD

The present disclosure relates generally to auxiliary surgical support appliances for operating room tables and, in particular, a modular distractor apparatus, system, and method specially adapted therefor, and arrangements of patient-supporting surfaces for specific parts of the body, including knees, and upper or lower legs.

BACKGROUND

With the advent of increasingly sophisticated surgeries for the knee, such as robotic and minimally-invasive surgeries, the requirements for precise bone and/or joint positioning are increasingly important to the overall success of the surgery and the patient's recovery and quality of life thereafter. A problem exists with conventional surgery systems in that the hardware and associated components lack the stability and distraction required by such surgeries. For example, surgical saws tend to cause the patient's limb to move as a bone is cut, especially when the structural rigidity of the support apparatus is inadequate. When the patient's limb moves and changes position mid-surgery, this presents a challenge for the surgeon who relies on precision tools to successfully conduct these advanced procedures without issue.

Such surgical limb-support systems present additional challenges. For example, such systems need to be easily sterilizable with components that are adapted to be placed and fit within conventional sterilizer systems. Also, these systems should provide the doctors and nurses who perform the surgery with a level of convenience suitable for use; such systems should therefore be adaptable to individual patient size, should at times allow for single-hand operation, and should free up the hands of nurses and support staff who would otherwise be required to hold objects for periods of time, such as the patient's open skin, during prolonged periods of the operation. Additionally, the number of parts and the complexity of the system present a challenge in that the amount of time required to assemble and/or disassemble the system directly affects important aspects of the overall procedure, such as time and cost.

For at least the reasons mentioned above, conventional surgery systems are subject to a variety of challenges.

Therefore, it would therefore be functionally and economically advantageous to provide a distractor system, such as a knee positioner system that overcomes these challenges.

SUMMARY

The present disclosure provides an apparatus, system, and method for positioning, holding, and/or distracting the bones and associated ligaments and tissue of the knee during surgery.

In one aspect of the present disclosure, a modular distractor system may provide enhanced structurally stability and support of a patient's limb, which may provide stability on the order of millimeters, resulting in a better outcome for the patient.

In one aspect of the present disclosure, a modular distractor system may be utilized, capable of tailoring the overall support system to the unique physical parameters of a particular patient and/or surgery.

In another aspect of the present disclosure, a modular distractor system is presented, which provides ease of use for doctors and nurses to assemble, position, distract, and/or disassemble the system and components thereof during and throughout a surgery.

In another aspect of the present disclosure, a modular distractor system may include a minimal number of parts and facilitated ease of sterilization, wherein the distractor system components are adapted to be placed and fit within conventional sterilizer systems, such as those having trays dimensioned 24"×11.5"×8" (depth, width, and height, respectively).

In another aspect of the present disclosure, a modular distractor system may include an adapter portion, configured to couple to different forms of carriage assemblies, base plates, and/or different OR table side rail configurations and associated support systems.

In another aspect of the present disclosure, a modular distractor system may include an adapter portion configured to rotate to or from an orthonormal angle, with respect to the plane formed by the operating table surface, to position, hold and/or a patient's knee at said angle.

In another aspect of the present disclosure, a modular distractor system may include a static adapter portion adapted to couple to a positioner pad separate and irrespective of a dynamic distractor component.

In another aspect of the present disclosure, a modular distractor system may include a distractor assembly having enhanced user capabilities, such as the incorporation of an adaptable release bracket.

In another aspect of the present disclosure, a modular distractor system may include a distractor having a driver rod assembly with a support figured to provide superior coupling to a positioner pad, resulting in improved stability of the patient's limb during surgery.

In another aspect of the present disclosure, a modular distractor system may include modular patient pad assemblies, which provide superior positioning, holding, and stability during surgery.

In yet another aspect of the present disclosure, a modular distractor system may include modular patient pad assemblies that provide superior coupling qualities at the pad-distractor interface, such that desirable positioning, holding, and stability may be obtained during surgery.

DESCRIPTION OF DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following Detailed Description, which is to be read in association with the accompanying drawings, which are incorporated in and constitute a part of this specification, show certain aspects of the subject matter disclosed herein and, together with the description, help explain some of the principles associated with the disclosed implementations, wherein:

FIG. 15 illustrates another side view of a distractor body thereof;

FIG. 16 illustrates another side view of a distractor body thereof;

FIG. 17 illustrates a bottom view of a distractor body thereof;

DETAILED DESCRIPTION

Figure 1:
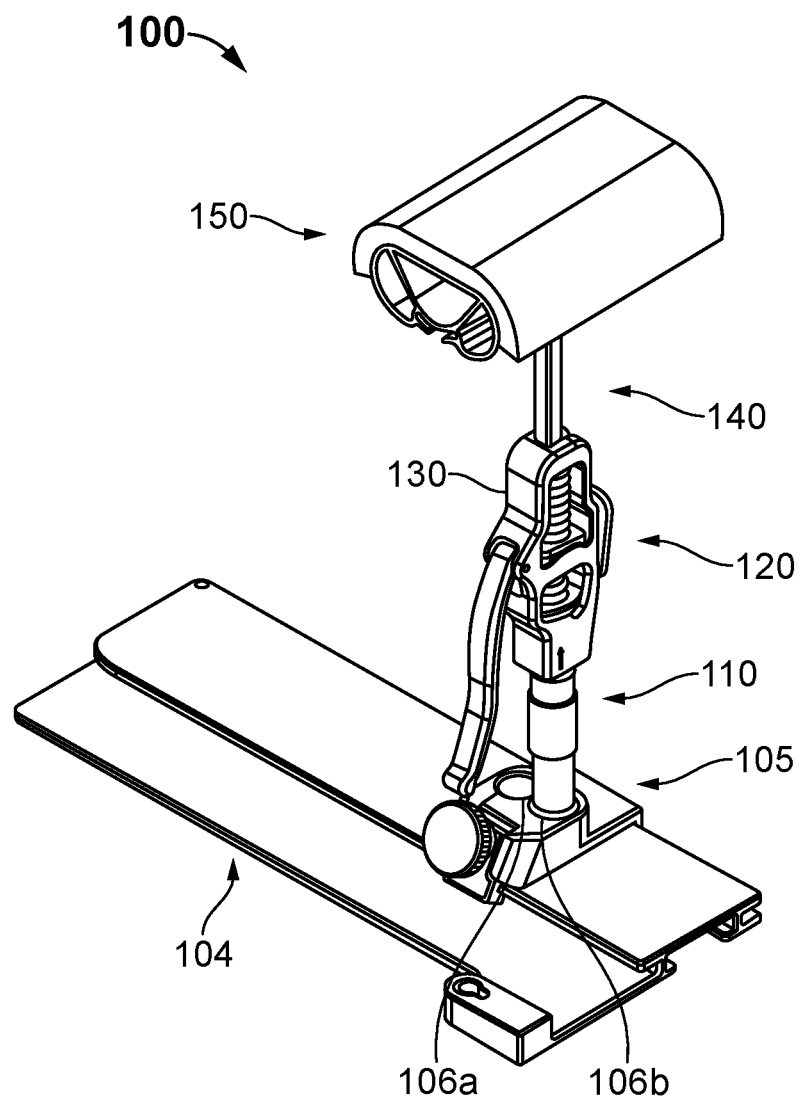
FIG. 1 illustrates a perspective view of a modular distractor apparatus, system, and method for supporting and securing specific parts of the body in accordance with an embodiment of the present disclosure.

Non-limiting embodiments of the invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present disclosure, and are not to be considered as a limitation thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As is illustrated in FIGS. 1-43, a modular distractor apparatus, system, and method is generally shown as element 100, which can provide the surgeon with a wide range of surgical support arrangements and applications, where like components, sub-assemblies, etc., as those described herein can be used to achieve similar objectives, and where the modularity of the components may provide the surgeon with a tailored structural support, to aid in achieving desired surgical results, such as the benefits described above.

Figure 23:
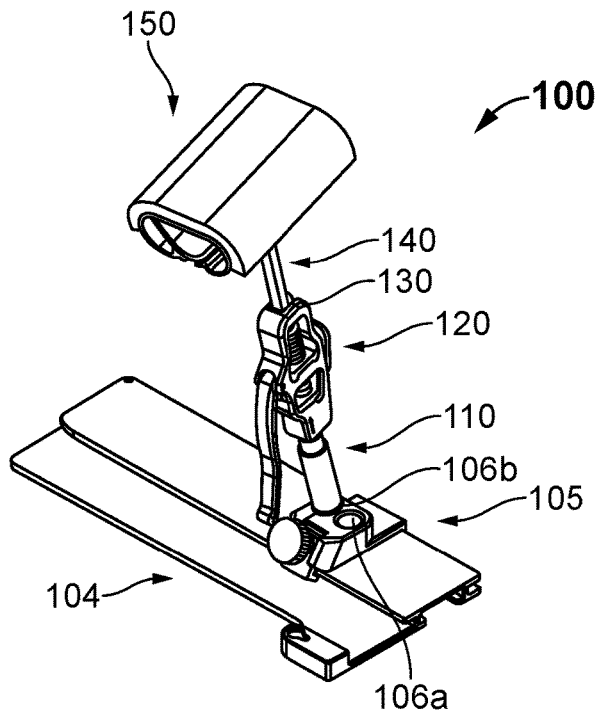
FIG. 23 illustrates a perspective view of a modular distractor apparatus, system, and method in accordance with an embodiment of the present disclosure.
Figure 24:
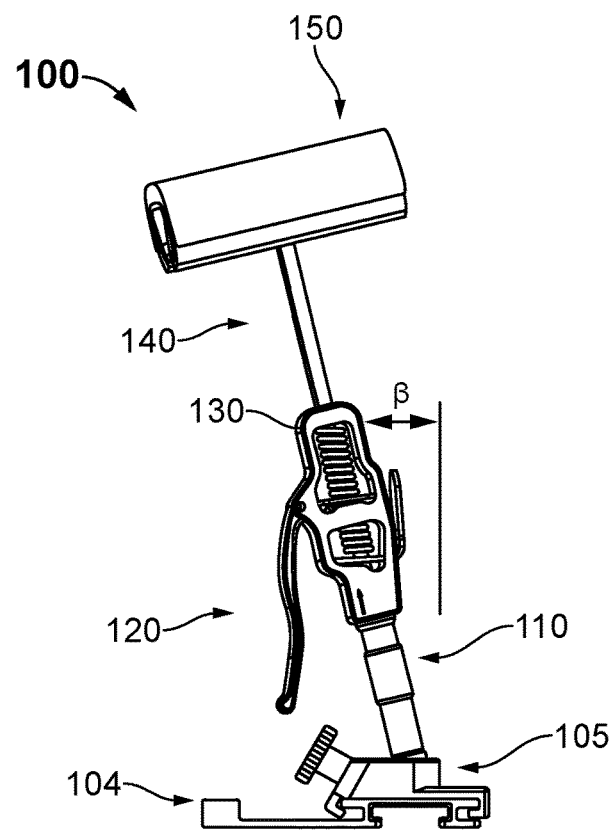
FIG. 24 illustrates a side view of a modular distractor apparatus, system, and method thereof.

FIG. 1 illustrates an exemplary preferred embodiment of a modular distractor apparatus, system, and method 100. The modular distractor 100 is configured to be set upon a support table or operating table (not shown) and secured thereto by coupling to a side rail (also not shown) either directly or indirectly. Indirect coupling of modular distractor 100 may be achieved via additional components such as a base plate assembly 104 and carriage assembly 105 as manufactured and offered for sale by Innovative Medical Products, Inc. under the product De Mayo Knee Positioner. As shown in FIGS. 1 and 23-24, carriage assembly 105 may include one or more openings such as a first carriage opening 106a, which may provide for a straight-vertical, tapered connection. Carriage assembly 105 may additional or alternatively provide for a second carriage opening 106b, which may provide for a tapered opening disposed at an offset angle β, as shown in FIG. 24. As shown, offset angle β may provide a rigid connection for the modular distractor 100 disposed at a range from about 10 degrees to about 15 degrees, relative to straight vertical. However, the offset angle β may be greater or less than said range, so as to be configured for a particular application and suited purpose. Furthermore, a third carriage opening 106c may provide for a ball-and-socket type connection so that modular distractor 100 may be disposed at, locked, or otherwise held at a multitude of discrete angles as may be desired.

FIG. 1 further illustrates that a modular distractor 100 may include an adapter portion 110, a distractor assembly 120 disposed within a distractor housing 130. The modular distractor 100 may further comprise a driver assembly 140 operably connected the distractor assembly 120 and distractor housing 130, where the distractor assembly 120 includes one or more biasing elements, a lock tab, a release tab, and handle that may be coupled to the distractor housing 130, to facilitate movement of the driver assembly 140 to position, distract, or otherwise hold the limb of a patient. At one end of the driver assembly 140 is a driver support that may be configured to couple to a positioner pad assembly 150, which may be configured to support the limb. In this manner and as shown, modular distractor 100 may be configured to provide the surgeon with alternative configurations by interchanging each sub-component assembly of the system, as may be desired to achieve an optimal positioning, holding and/or securing based upon a given patient's size and limb length/geometry, or for a combination suitable for given surgical procedure or objective.

Figure 2:
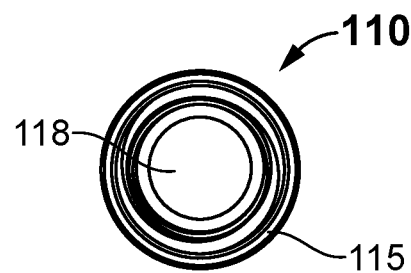
FIG. 2 illustrates a top view of an adapter portion in accordance with an embodiment of the present disclosure thereof.
Figure 3:
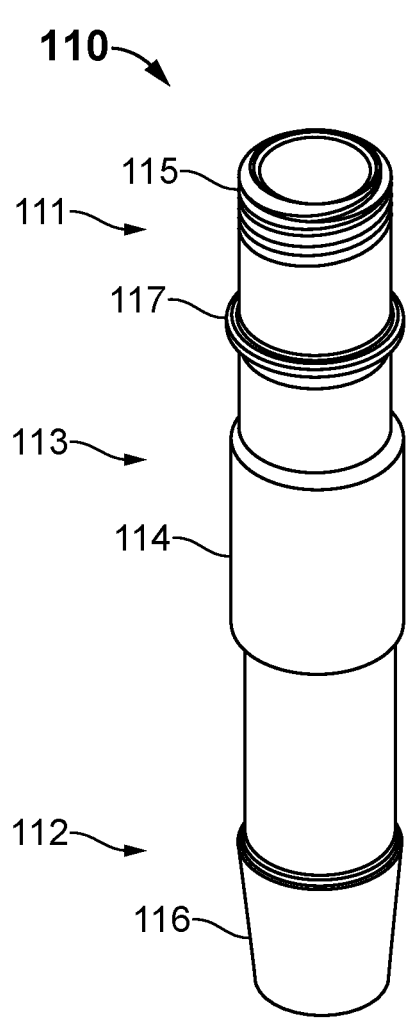
FIG. 3 illustrates a perspective view of an adapter portion thereof.
Figure 4:
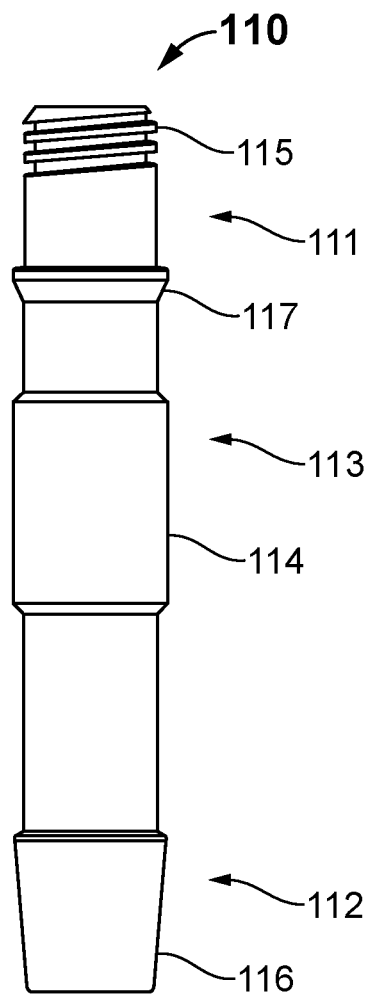
FIG. 4 illustrates a side view of an adapter portion thereof.

Referring now to FIGS. 1-4 an embodiment of an adapter portion 110 is provided. Referring to FIGS. 2, 3 and 4, the adapter portion 110 may include a first end 111, a second end 112, and a middle portion 113 disposed therebetween. A handle portion 114 may be disposed along a portion of the length of the adapter 110, and may be configured with texture such as knurled to provide the surgeon with a frictional grip sufficient to securely install, assemble, disassemble, or otherwise couple adapter portion 110 as desired. Second end 112 may be provided with a tapered portion 116, configured to operably connect to said first and/or said second carriage openings 106a and 106b, respectively, as described above and shown in FIGS. 1 and 23-24. Tapered portion 116 may be formed at any angle of inclination suitable to provide a sufficient holding effect between the adapted portion 110 and the carriage assembly 105. Alternatively, second end 112 may be straight, i.e., non-tapered, or may be formed with a ball (not shown) to form a ball-and-socket connection as previously described. First end 111 may include a threaded portion 115 and/or a shelf portion 117, which are configured to securely couple and hold the adapter portion 110 to a distractor assembly 120. Additionally, as shown in FIG. 2, adapter portion 110 may include an opening 118, formed through at least a portion of the length thereof, i.e., formed from the first end 111 and extending downwardly toward the second end 116. As will be further described below, the opening 118 may be configured to provide sufficient clearance for a driver rod 141 to pass through opening 118 so that, in operation, the distractor assembly 120 and distractor housing 130 can perform the function of raising and lowering which, in turn, performs the function of positioning, securely holding, and/or distracting the limb of the patient during surgery.

Figure 5:
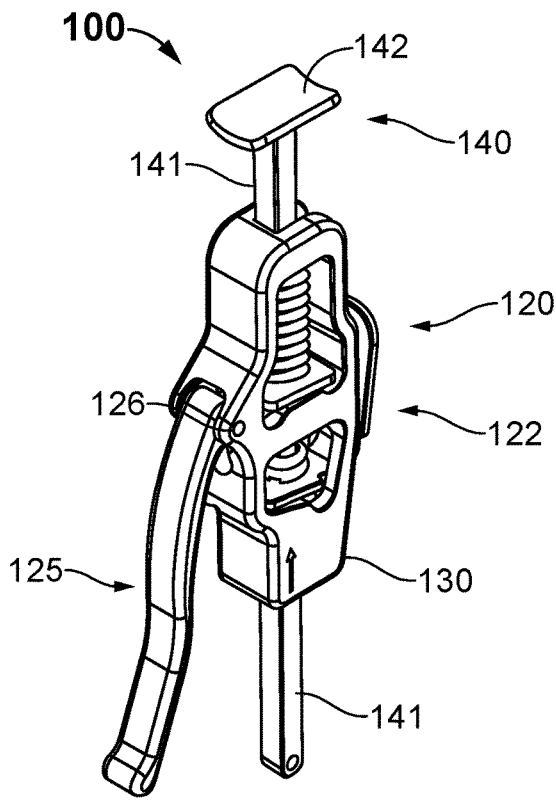
FIG. 5 illustrates a perspective view of a distractor assembly in accordance with an embodiment of the present disclosure.
Figure 6:
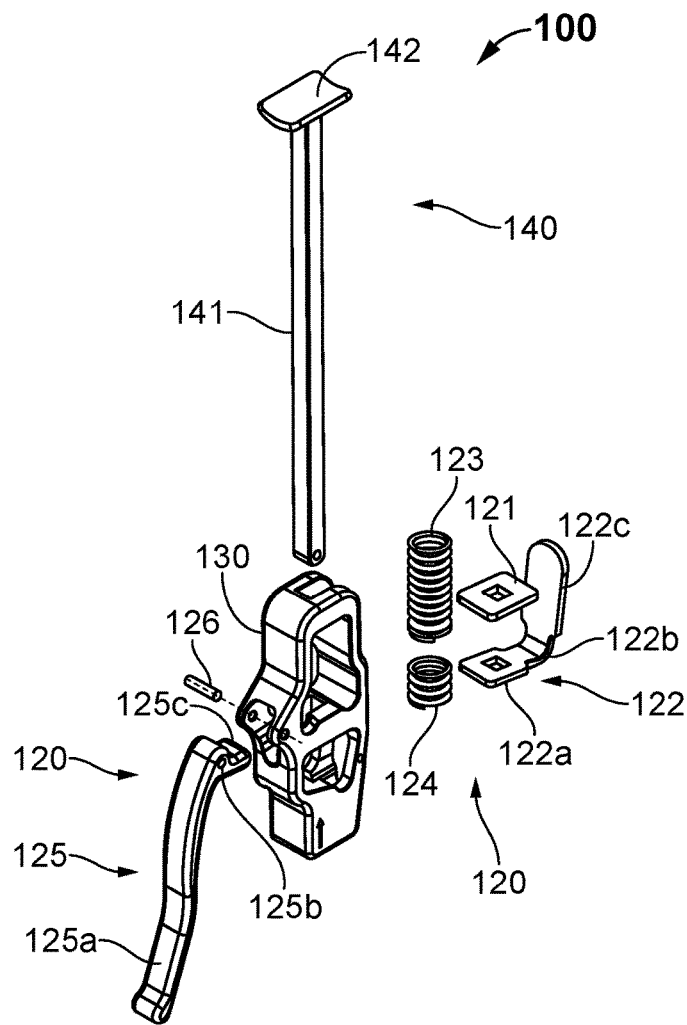
FIG. 6 illustrates an exploded perspective view of a distractor assembly thereof.

Referring now to FIGS. 5 and 6, a distractor assembly 120 may include components that fit within, and operably connect to, distractor housing 130, in a manner that achieves the desired objective of raising, holding or lowering the position of a driver support 142 of driver assembly 140, relative to the plane formed by the surface of the support and/or operating room table. As shown in FIG. 6, the distractor assembly 120 may comprise an extension bracket 121, a release bracket 122, one or more biasing elements such as a compression spring 123 for advancing the driver rod 141, one or more biasing elements such as an extension spring 124 for selectively releasing the driver rod 141 from a fixed position, and a lever 125. As illustrated in the accompanying description of FIGS. 7-10, in operation the distractor assembly 120 achieves a desired effect of raising, holding, and/or lowering driver assembly 140 via operative communication with driver rod 141. Driver rod 141 may be of uniform cross-sectional dimension, so that it is configured to pass through distractor housing 130, and couple to the components comprising distractor assembly 120.

In operation, the surgeon may apply selective force to the lever 125 of modular distractor 100 to achieve a desirable effect. For example, in the assembled configuration demonstrated in FIG. 5, as specifically illustrated in FIG. 6, an appropriate force may be applied along a contact portion 125a of lever 125, causing level 125 to pivot about a pivot portion 125b. In an assembled configuration, lever 125 may operably couple to distractor housing 130 via a pivot pin 126. The applied force thereby raises driver portion 125c that operably connects to change the angular orientation of the extension bracket 121 with respect to other components of the system, such as, for example, driver rod 141 and/or distractor housing 130. Similarly, in the assembled configuration shown in FIG. 5 and FIG. 6, an appropriate force may be applied along a contact release portion 122c of release bracket 122, causing the same to pivot about a curved portion 122b. In effect, the applied force along contact release portion 122c changes the angular orientation of 122a with respect to other components of the system such as, for example, driver rod 141 and/or distractor housing 130.

The extension bracket 121 and the release bracket 122 each comprise openings configured to accept driver rod 141 along discrete locations of its length. When the extension bracket 121 and the release bracket 122 are disposed in a plane substantially normal, orthogonal and/or perpendicular to an axis formed by the length of the driver rod 141, whereby each of the respective openings allow for uninhibited movement of the driver rod 141 therethrough. Equally, movement of the driver rod 141 is inhibiting by one or more edges of the openings in the extension bracket 121 and/or the release bracket 122 so as to operably couple to the driver rod 141 when either the extension bracket 121 or the release bracket 122 becomes disposed in a manner that is not substantially orthogonal to an axis of the driver rod 141. The biasing elements of each of the compression and extension springs 123, 124, respectively, operably apply forces on each of the extension bracket 121 and/or the release bracket 122 to facilitate movement actions of brackets 121, 122.

Figures 7, 8, 9, 10:
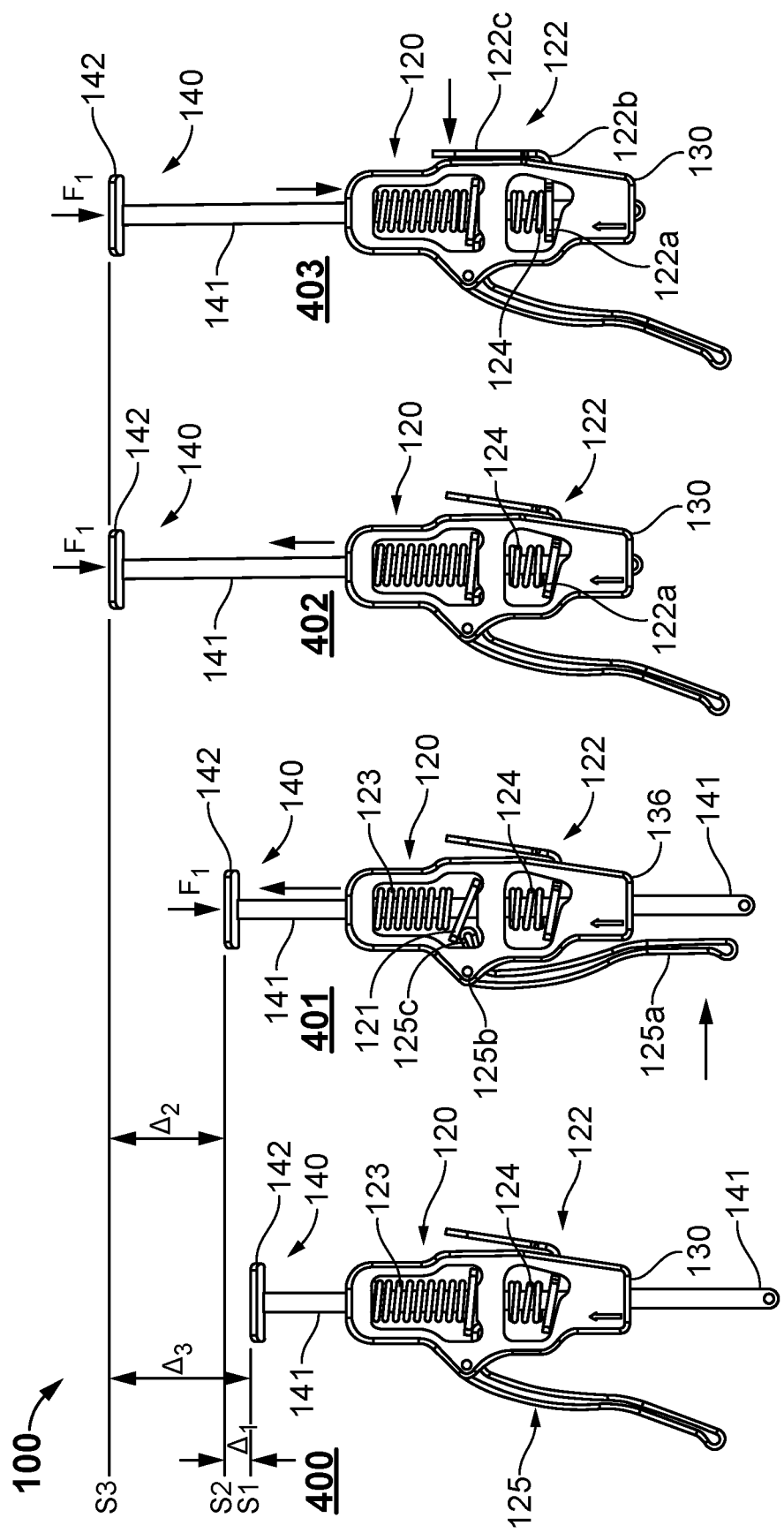
FIG. 7 illustrates a side view of a distractor assembly in a first position thereof.
FIG. 8 illustrates a side view of a distractor assembly in a second position thereof.
FIG. 9 illustrates a side view of a distractor assembly in a third position thereof.
FIG. 10 illustrates a side view of a distractor assembly in a fourth position thereof.

Referring now to FIGS. 7-10, relative positioning of certain components comprising modular distractor 100 may be observed. FIG. 7 shows modular distractor 100 wherein driver support 142 is positioned at a first height, S1. First height S1 represents a configuration where the height of driver assembly 140 may be sufficiently withdrawn to allow adequate clearance for the surgeon to install or otherwise position modular distractor 100, in preparation for extending the same to achieve a holding or distracting position of the patient's limb. Here, neither extension bracket 121 nor release bracket 122 necessarily inhibit movement of driver assembly 140.

Figure 18:
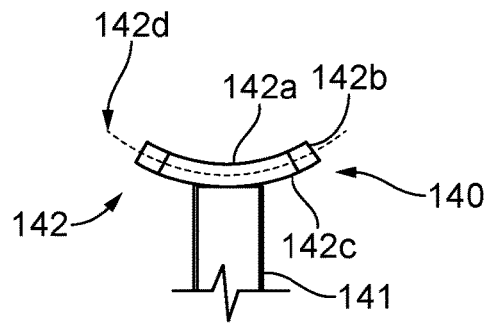
FIG. 18 illustrates a side view of a driver assembly in accordance with an embodiment of the present disclosure.

Referring to FIG. 8, a force is applied along contact portion 125a in the direction indicated. Driver portion 125c then contacts a portion of extension bracket 121, causing the same to change angular orientation. Edges of the opening formed by extension bracket 121 then operably communicate with driver rod 141, causing driver support 142 to move by distance $\Delta_1$ to position S2, wherein modular distractor 100 is preloaded with a force $F_1$. Force $F_1$ acts generally normal to the surface formed by support top 142a, as shown in FIG. 18. In the preloaded position S2 according to FIG. 8, $F_1$ acts in a downward direction, and is meant to represent the weight of the limb of the patient; however, the resultant force acting on modular distractor 100 may change depending on the height of driver support 142 when modular distractor 100 is under load, as may be affected by associated tensions and other external forces. Importantly, the motion of driver rod 141 caused by action of the lever 125 ensures that release bracket 122 decouples from driver rod 141, so long as extension bracket 121 acts upon driver rod 141. During this action, extension spring 124 acts upon release bracket 122 so that it assumes a substantially orthonormal position relative to the axis formed by the length of driver rod 141. The process of pumping lever 125 may be repeated so that the desired holding and/or distracting position is achieved. Similarly, the level 125 may be only partially pumped, so that the desirable height is more finely-tuned.

Referring to FIG. 9, lever 125 reassumes the position shown in FIG. 7, thus engaging release bracket 122 to maintain a position S3 at a distance 43 while the modular distractor 100 remains under load F1. In this way, release bracket 122 provides a resistive, locking force of driver rod 141 sufficient to hold the modular distractor 100 at position S₃. Notably, in this configuration extension bracket 121 becomes disengaged, or substantially orthonormal relative to the axis formed by the length of driver rod 141, due to the force and positioning of compression spring 123. In particular, compression spring 123 assures that extension bracket 121 reassumes its original position once level 125 is released, ensuring that bracket 121 disengages with driver rod 141.

Referring to FIG. 10, release bracket 122 is engaged by applying a force along the contact release portion 122c in the direction indicated. In this configuration, while modular distractor 100 remains under a force $F_1$, driver assembly 140 is retracted from its height at position S3 to a different location. As may be desirable at a certain stage of the operation, once the patient's limb has been maintained in a distracted position and the work completed at position S2, modular distractor 100 may be released so that the patient's limb can assume its natural position. Here, as shown in FIG. 10, both brackets 121, 122 maintain substantially orthonormal orientations, thereby allowing free movement of driver rod 141 through driver housing 130 and driver assembly 120.

FIGS. 7-10 may be described in terms of method steps typically illustrative of that which may be desirable in a surgical application. In a first step 400, modular distractor 100 may be configured to position driver support 142 at a height S1, corresponding to a sufficiently retracted position to install/assemble modular distractor 100 about a limb of a patient, in preparation for surgery. In a second step 401, distractor module 100 may be pumped, by applying a force, in the direction indicated in FIG. 7, about contact portion 125c, resulting in an outward/upward movement of driver support 142 such that modular distractor 100 becomes subject to a force $F_1$, located at a position S1 at a distance $\Delta_1$. In a third step 402, modular distractor 100 may be configured to maintain a position S3 at a distance $\Delta_2$ (from S2) or a distance $\Delta_3$ (from S1), the position S3 corresponding to a holding, supporting or distracting position of the patient limb. In a fourth step 403, modular distractor 100 may be configured such that contact release portion 122c of release bracket 122 is depressed in the direction indicated, thereby releasing driver rod 141 from a holding position, resulting in a lowering, or contracting, of modular distractor 100 and of driver support 142 in particular.

FIGS. 11-17 illustrate an embodiment of the distractor housing 130 of the modular distractor 100. In general, distractor housing 130 is configured to easily disassemble, sterilize, and reassemble the components coupled thereto, which may include the adapter portion 110, the component comprising the distractor assembly 120 and the driver assembly 140. The distractor housing 130 therefore provides a design having smooth transitions, such as chamfered and/or filleted edges that work to minimizes residual bacterial deposits that may accumulate due to the modular distractor 100 being within the sterile field of surgery. It should be observed that all components comprising modular distractor 100 employ similar design feature. As best seen in FIG. 15, distractor housing 130 therefore may comprise a distractor body 131 including first and second body cavity portions 132, 133, respectively. And as most easily seen in FIG. 6, body cavity portions 132, 133 provide for easy insertion and assembly of distractor assembly 120, including compression spring 123, extension spring 124, extension bracket 121, release bracket 122, and driver rod 141, which may be threaded therethrough. An indicator arrow shown on distractor body 131 may aid the user by illustrating a functional direction to ensure proper assembly of modular distractor 100 after sterilization, or in preparation for use.

Figure 11:
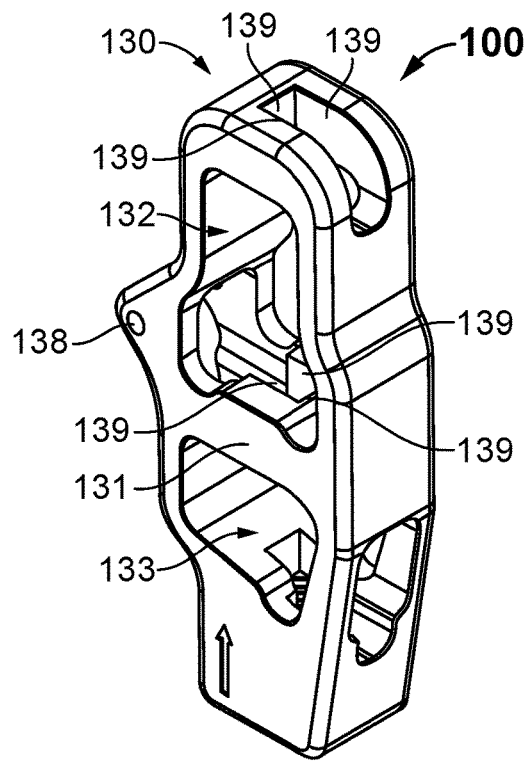
FIG. 11 illustrates a top-down perspective view of a distractor body in accordance with an embodiment of the present disclosure.
Figure 12:
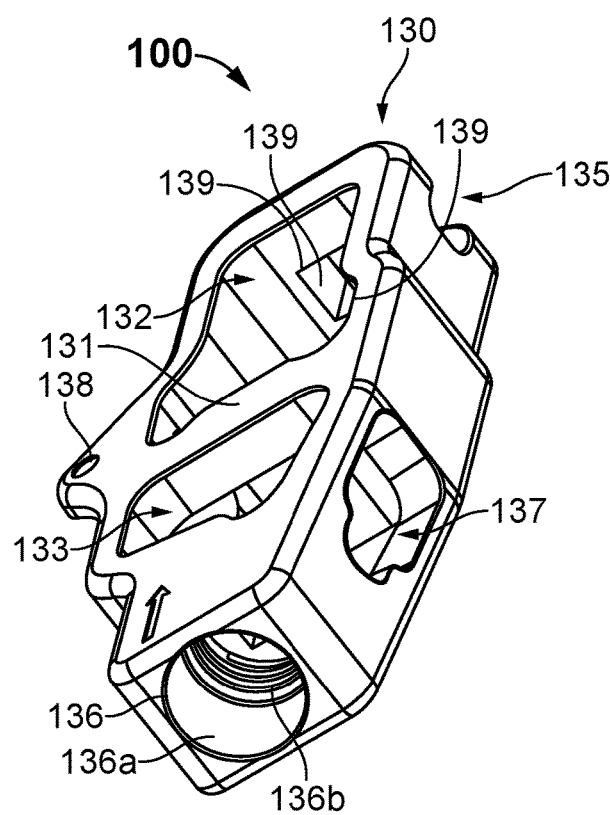
FIG. 12 illustrates a bottom-up perspective view of a distractor body thereof.
Figure 13:
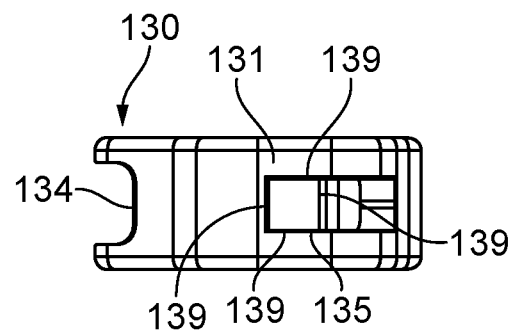
FIG. 13 illustrates a top view of a distractor body thereof.

As can be seen at various orientations throughout FIGS. 11-17, additional openings within distractor housing 130 provide access to, and positioning of, other components of distractor assembly 120. A lever opening 134 may be configured to accept lever 125. An upper opening 135 may be configured to accept driver rod 141. A lower opening 136 may be configured to accept adapter portion 110. A release opening 137 may be configured to accept release bracket 122. Additionally, a pivot pin opening 138 may be configured to accept pivot pin 126. As shown in FIG. 12, lower opening 136 may comprise non-threaded portion 136a and threaded portion 136b. Importantly, these features of lower opening 136 complement features of adapter portion 110, as shown in FIGS. 3 and 4. Shelf portion 117 may couple to the lower extent of distractor body 131 to help ensure cross-threading does not occur, and/or to provide additional stability to the coupled components 110, 130, once assembled.

Figure 14:
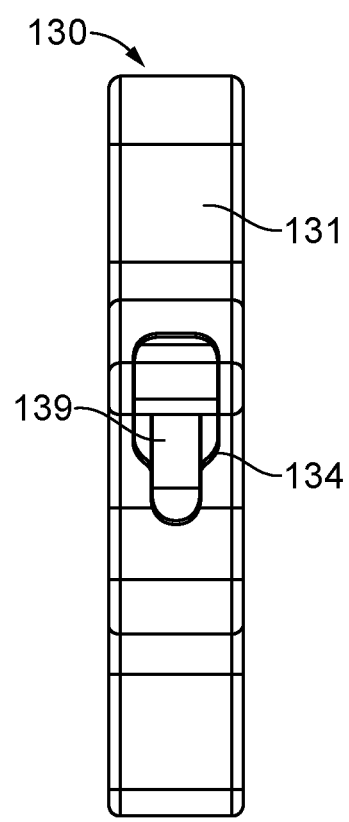
FIG. 14 illustrates a side view of a distractor body thereof.

FIGS. 11-14 illustrate the distractor housing 130, and FIGS. 16-17 also show at various locations a driver rod profile 139, which may be configured to confine a driver rod 141 to a single degree of freedom when it is assembled within distractor housing 130. Advantageously, driver rod 141 may take any shape, such as substantially square as shown, or cylindrical. In a cylindrical embodiment, distractor body 131 would employ cylindrical driver rod profiles 139 to constrain driver rod 141 to two degrees of freedom. In the embodiment shown, driver rod profile 139 may be partially embedded within upper opening 135 as shown in FIGS. 11-12 and 16, within the interstitial space separating first and second body cavity portions 132 and 133 as shown in FIGS. 11 and 14, and within lower opening 136 as shown in FIGS. 11-13, and 16-17. As best seen in FIG. 11, driver rod 139 alternates from the left side of upper opening 135, to the right side of the interstitial space formed between body cavity portions 132 and 133, and then back to the left side of lower opening 133. Applying the principle of kinematic constraint, this arrangement accomplishes the precise number of contact points needed to allow the desired degree of freedom without over-constraining the driver assembly 140, which minimizes the potential for structural rigidity issues to arise, due to, for instance, errors from manufacturing tolerances.

Figure 19:
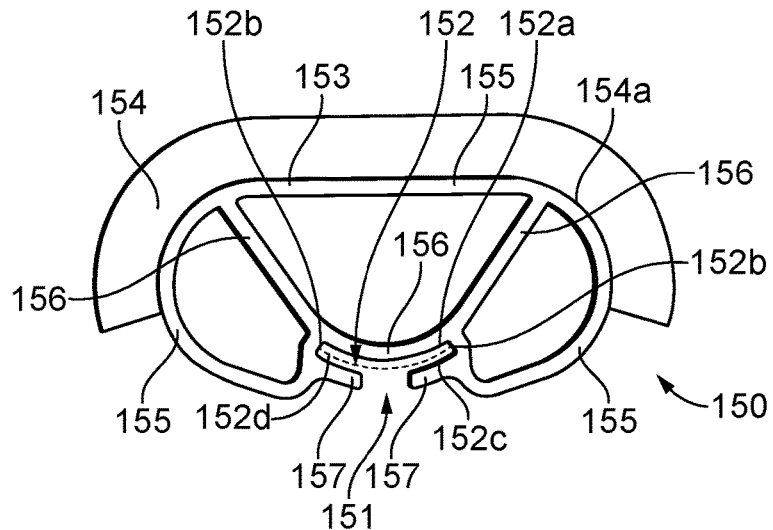
FIG. 19 illustrates a side view of an extruded positioner pad assembly in accordance with an embodiment of the present disclosure.

Referring now to FIGS. 18-22, certain aspects of the driver assembly 140 and positioner pad assembly 150 are shown. FIG. 18 shows that driver assembly 140 may comprise driver rod 141 and driver support 142 rigidly affixed thereto. Driver support 142 may comprise a support top 142a, a support side 142b, a support bottom 142c, and a support profile 142d. Turning to FIG. 19, an embodiment of the positioner pad assembly 150 is shown comprising a two-dimensional, extruded shape that provides ease of manufacturing and lower costs. Here, positioner pad assembly 150 may comprise a driver rod cavity 151 and a support cavity 152 including a corresponding top, sides, and bottoms 152a, 152b, and 152c respectively. Support cavity 152 may further comprise an extruded support profile 152d. Importantly, in-kind features of driver support 142 correspond to in-kind features of positioner pad assembly 150, to advantageously provide improved coupling capability of the positioner pad assembly 150 to the other components of modular distractor 100, which facilitate improved structural rigidity, while maintaining modular capabilities of the system to accommodate a tailored approach to specific surgical applications.

In the embodiment of FIG. 19, positioner pad assembly 150 may further comprise a positioner body 153, which made of high impact styrene material, or any other material that meets strength, impact resistance, and heat resistance requirements associated with surgical applications. While positioner pad assembly 150 is generally configured to be one-time use in operation, multiple use pad assemblies are also within the scope of this disclosure. Positioner body 153 is formed in a two-dimensional shape for ease of production in an extruded manufacturing process. Positioner body 153 therefore may generally comprise a variety of structural configurations suitable for surgical applications; as shown in FIG. 19, these may include peripheral support 155, one or more interior supports 156, and one or more lip supports 157. Surrounding at least a portion of positioner body 153 along an interface 154a formed at a surface of peripheral support 155 is a pad 154. Pad 154 made be made of foam, or any other material that meets strength, elasticity, and heat resistance requirements associated with surgical applications. Pad 154 may be coupled to positioner body 153 along interface 154a by an adhesive, or by any another method suitable for the intended purpose.

Figure 20:
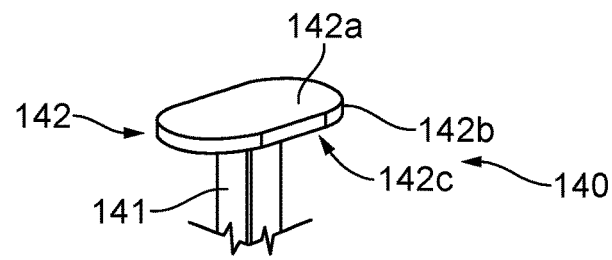
FIG. 20 illustrates a perspective view of a driver assembly thereof.

In the embodiment shown in FIG. 18, support profile 142d forms an arcuate, semi-circular, circular, or other curved profile. In an alternative embodiment, as shown in FIG. 20, the corresponding support profile 142d may be substantially straight. Support profile 142d may alternatively be convex or concave, or may be formed as an "M" shape, a zig-zag shape, or any other equivalent structured shape that provides adequate stability and structural rigidity suitable for surgical support applications.

Figure 21:
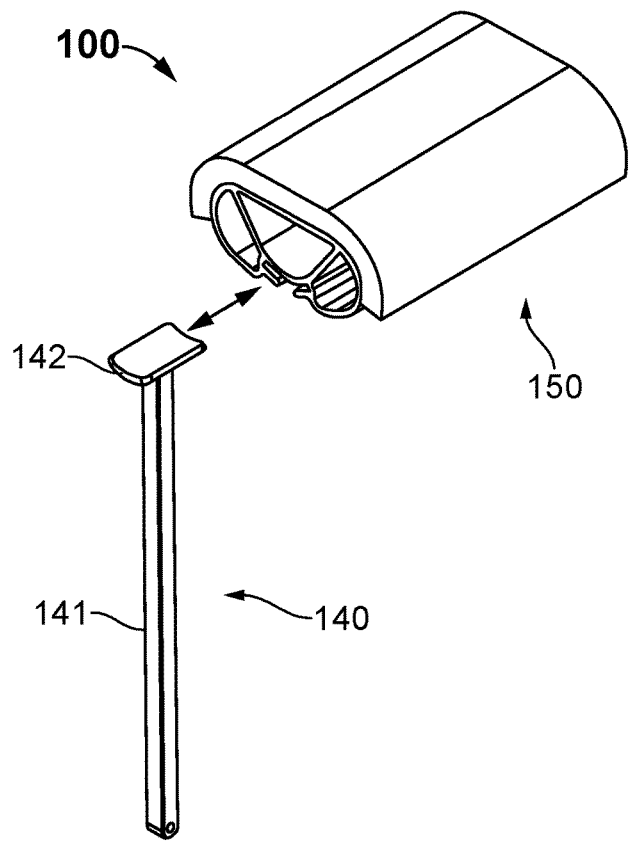
FIG. 21 illustrates a top-down perspective view of a driver assembly and an extruded positioner pad assembly thereof.
Figure 22:
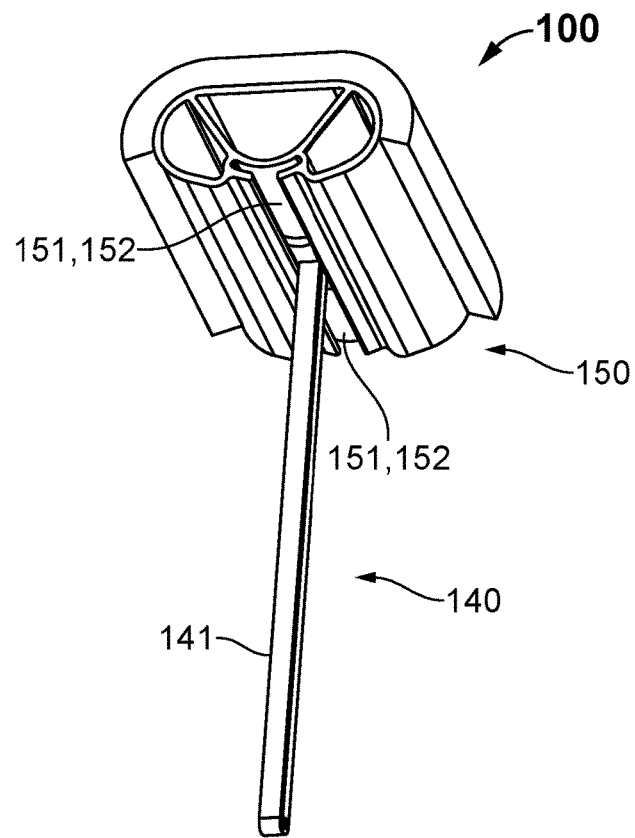
FIG. 22 illustrates a bottom-up perspective view of a driver assembly and an extruded positioner pad assembly thereof.

In operation, as generally depicted in FIGS. 21 and 22, driver support 142 and/or driver rod 141 may be configured to couple to positioner pad assembly 150 by sliding driver rod assembly into cavities 151, 152. As shown in FIG. 22, driver assembly and positioner pad assembly 150 frictionally-engage to provide adequate holding and structural support, while simultaneously providing adequate conformity to the contours of the patient's limb to provide holding, positioning, and distracting thereof. For instance, the driver support 142, as facilitated by the embodiment support profile 142d shown in FIGS. 21 and 22, prohibits rotation of the positioner pad on account of the support top, sides, and/or bottom and their in-kind coupling to corresponding portions of positioner body 153.

Referring to FIGS. 23 and 24, an assembled embodiment of modular adapter 100 is shown. Here, as previously described, angle β and the corresponding second carriage opening 106b into which adapter portion 110 may be inserted, generally serves the purpose of providing the surgeon with an alternative secure support configuration that works on the principle that a patient's leg tends to fall outwardly toward the edge/side rail 102 of an operating table 101 when the patient is in the supine position. Therefore, modular distractor 100 in an embodiment that utilizes angle and the corresponding second carriage opening 106b negates this tendency by providing appropriately-angled support.

Figure 25:
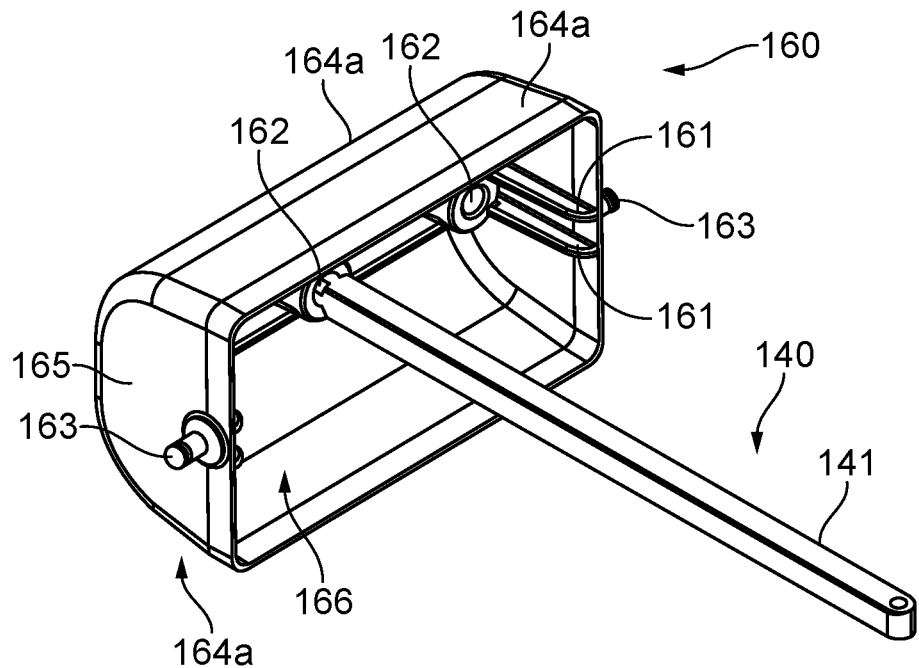
FIG. 25 illustrates a perspective view of a driver assembly and an injection-molded position pad assembly in accordance with an embodiment of the present disclosure.
Figure 26:
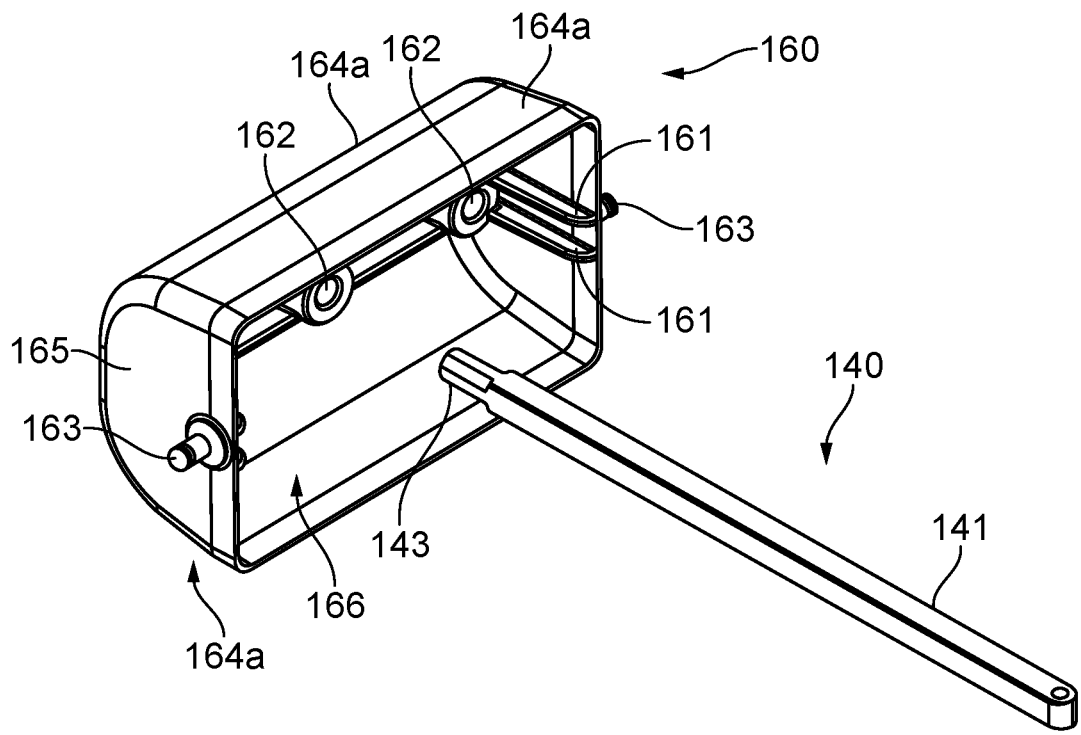
FIG. 26 illustrates an exploded perspective view of a driver assembly and an injection-molded position pad assembly thereof.
Figure 27:
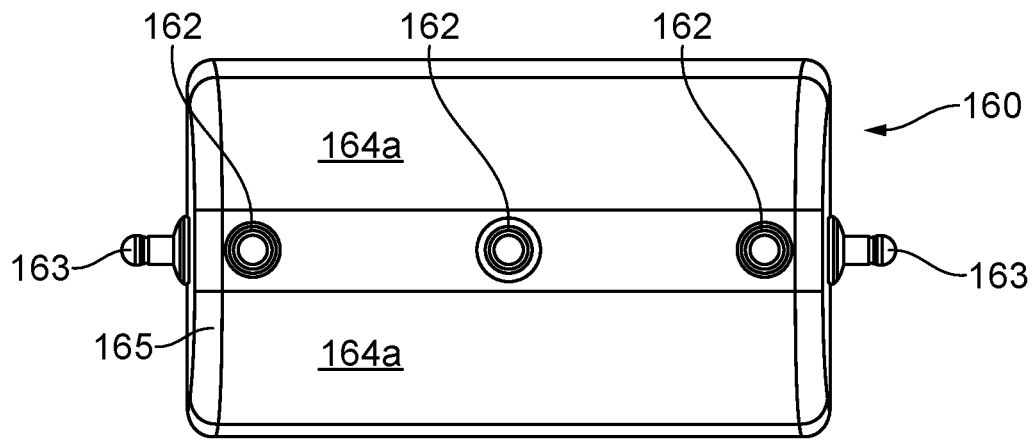
FIG. 27 illustrates a top view of a driver assembly and an injection-molded position pad assembly thereof.
Figure 28:
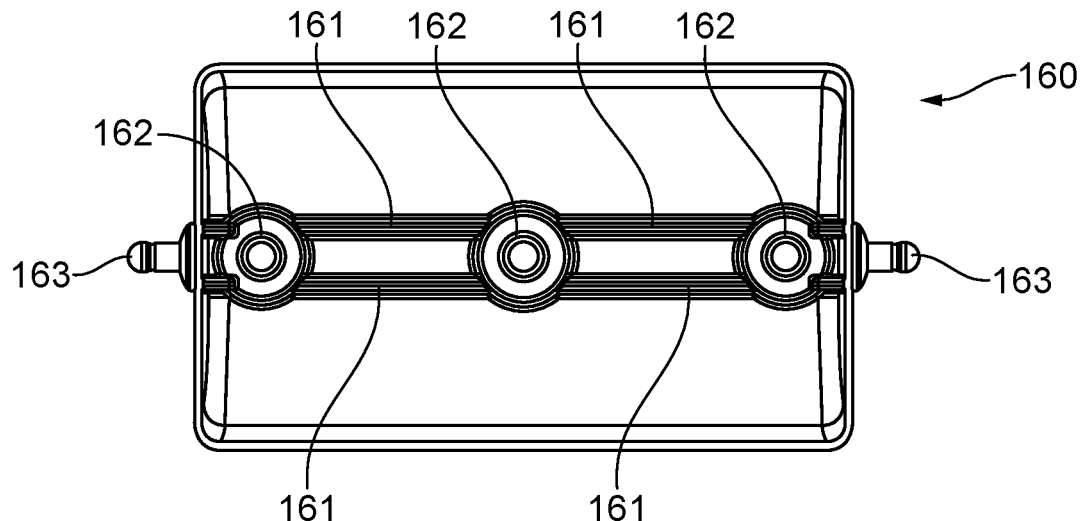
FIG. 28 illustrates a bottom view of a driver assembly and an injection-molded position pad assembly thereof.
Figure 29:
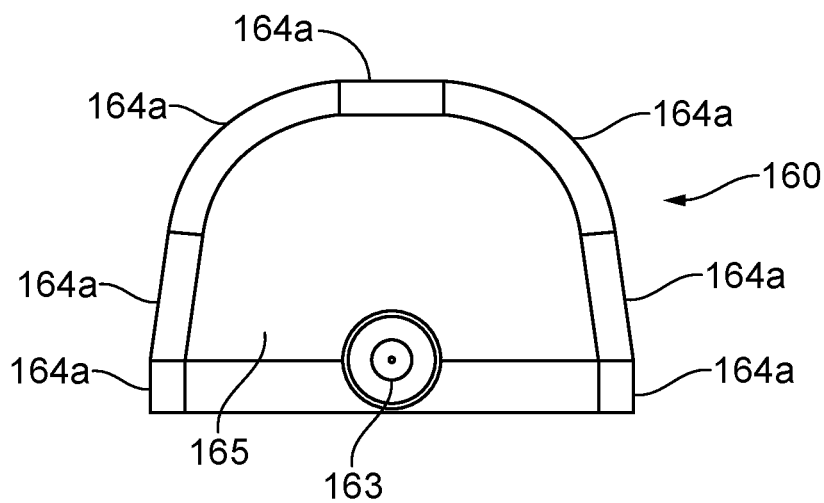
FIG. 29 illustrates a side view of a driver assembly and an injection-molded position pad assembly thereof.
Figure 30:
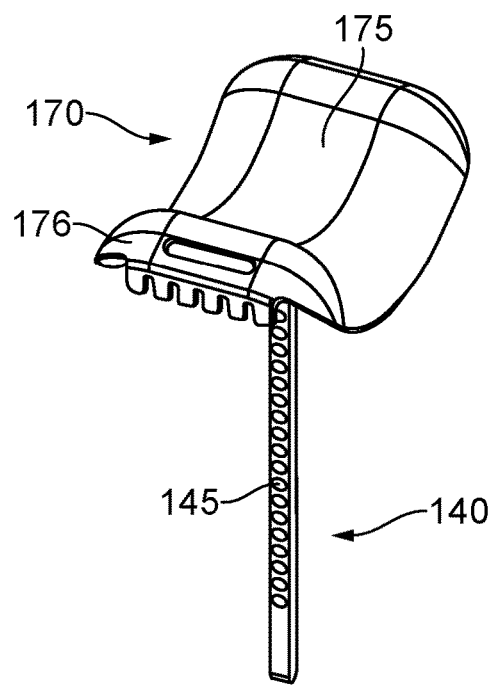
FIG. 30 illustrates a top-down perspective view of a driver assembly and an injection-molded position pad assembly thereof.

Referring to FIGS. 25-29, an alternative embodiment of driver rod assembly 140 and a positioner pad assembly 160 is described. As illustrated in FIG. 26, driver rod assembly 140 may alternatively comprise a driver rod support 143, which may be generally cylindrical, octagonal, or polygonal shaped. Support 143 may couple to a first injection-molded positioner pad assembly 160 at any one of support openings 162 via a snap on connection, as shown in FIG. 25. Assembly 160 may be made of high impact styrene or other suitable material, may be formed by an injection-mold process forming exterior surface 165 and interior cavity 166, and may be one-time use/disposable. Assembly 160 may further comprise one or more support ribs 161, and one or more support projections 163, the latter being configured as an anchor point for retractors to hold the patient's skin open during surgery, thus advantageously freeing up the hands of a nurse or other surgical personnel. A pad 164 (not shown)

made of foam or other suitable material may be disposed on at least a portion of the surface formed along interface 164*a*, affixed thereto via an adhesive or other suitable method.

Figure 31:
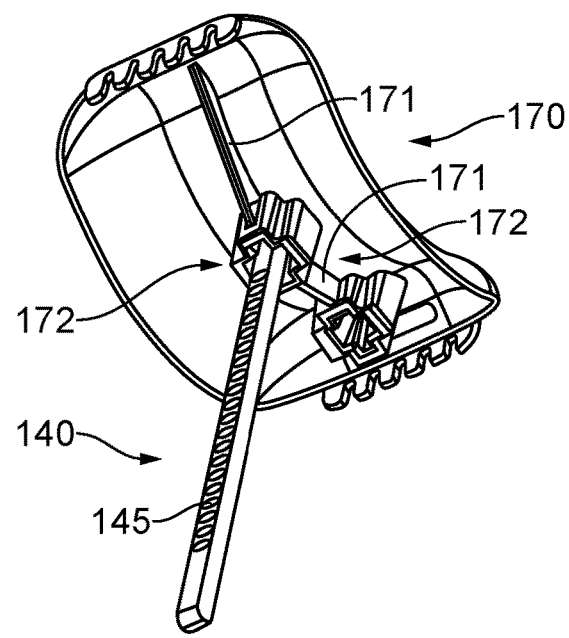
FIG. 31 illustrates a bottom-up perspective view of a driver assembly and an injection-molded position pad assembly thereof.
Figure 32:
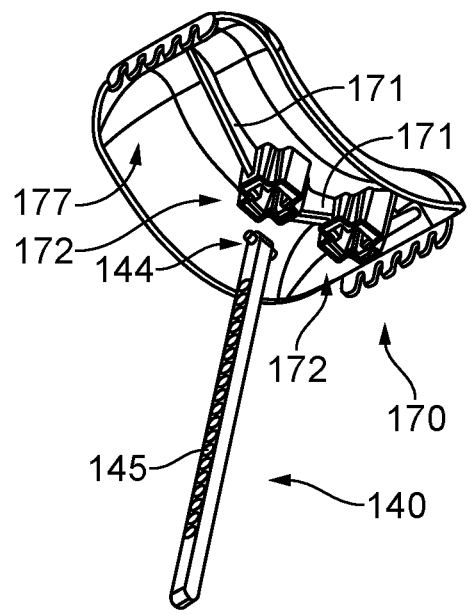
FIG. 32 illustrates an exploded bottom-up perspective view of a driver assembly and an injection-molded position pad assembly thereof.
Figure 33:
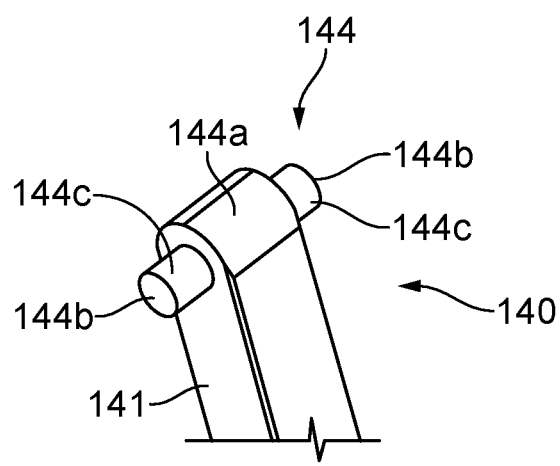
FIG. 33 illustrates a perspective view of a driver assembly thereof.
Figure 34:
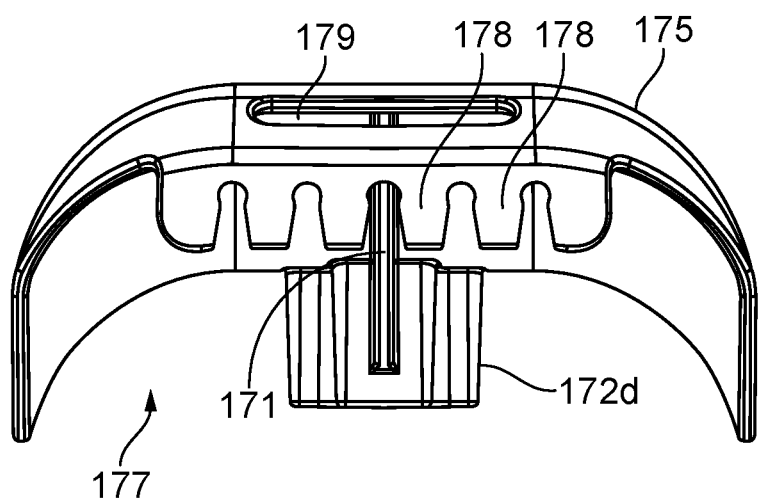
FIG. 34 illustrates a side view of an injection-molded position pad assembly thereof.
Figure 35:
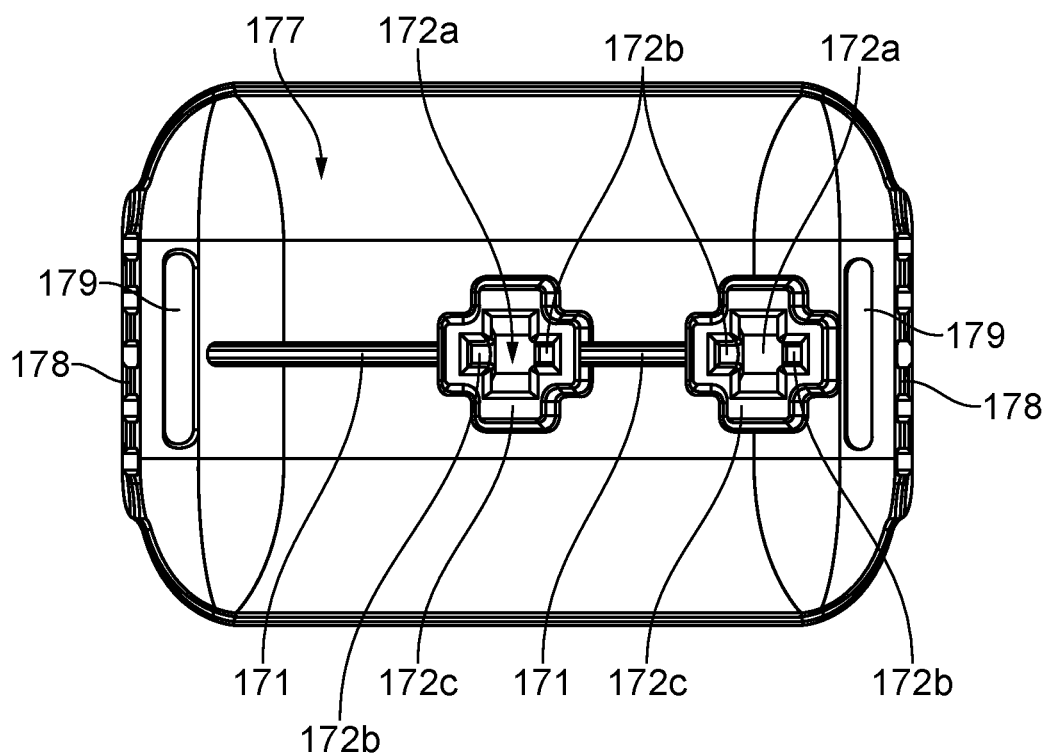
FIG. 35 illustrates a bottom view of an injection-molded position pad assembly thereof.
Figure 36:
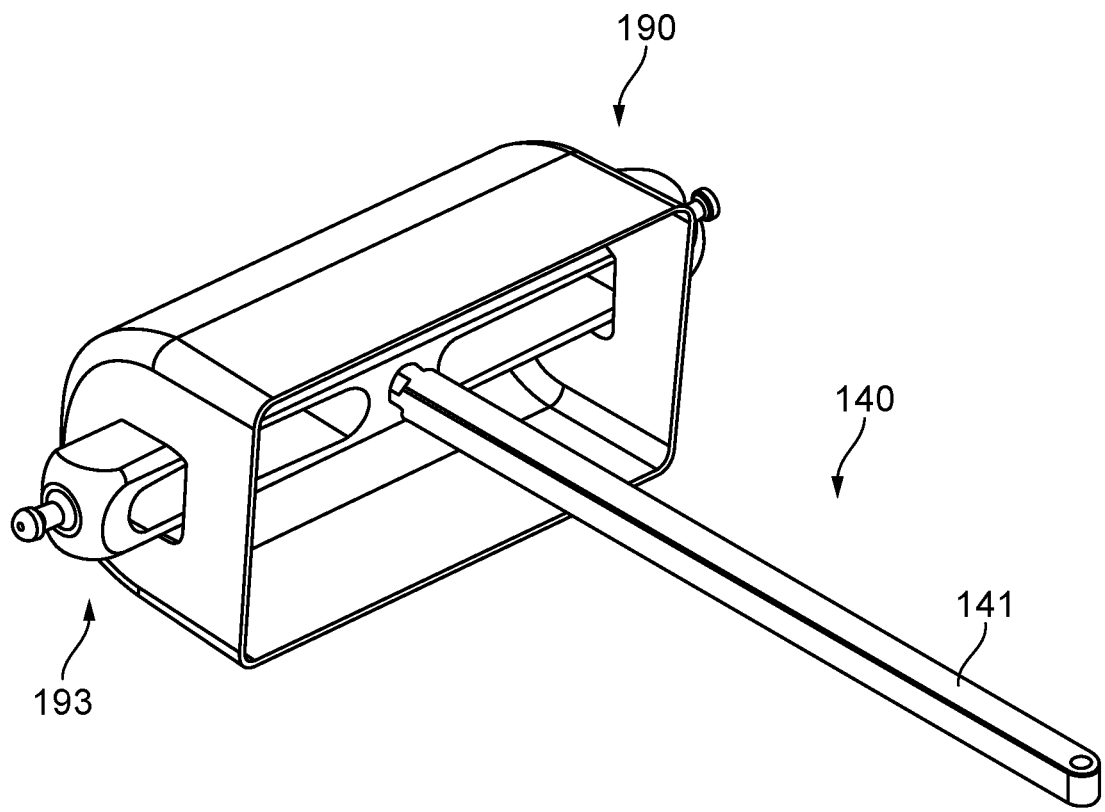
FIG. 36 illustrates a perspective view of an injection-molded position pad assembly thereof.

Referring to FIGS. 30-35, another alternative embodiment of driver rod assembly 140 and a positioner pad assembly 170 is provided. As illustrated in FIGS. 32-33, a driver rod assembly 140 may alternatively comprise a driver rod support 144, which may have a substantially rotatable profile 144*a*, features 144*b* that may have a feature profile 144*c* forming protrusions, intrusions, or other similarly shaped entities that facilitate the objection of providing a degree of rotation capability between driver rod assembly 140 and positioner pad assembly 170, when assembled. Support 144 may couple to a second injection-molded positioner pad assembly 170 at any one of support openings 172 via a snap on connection, as shown in FIG. 31. Assembly 170 may be made of high impact styrene or other suitable material, may be formed by an injection-mold process forming exterior surface 176 and interior cavity 177, and may be one-time use/disposable. Assembly 170 may further comprise one or more support ribs 171, and one or more teeth 178, the latter being configured as an anchor point for retractors to hold the patient's skin open during surgery, thus advantageously freeing up the hands of a nurse or other surgical personnel. A pad 174 (not shown) made of foam or other suitable material may be disposed on at least a portion of the surface formed along interface 175, affixed thereto via an adhesive or other suitable method. As best seen in FIGS. 34 and 35, support openings 172 may include a receiver body 172*c* having a depth 172*d*, rotatable profile receiver 172*a*, one or more feature receivers 172*b*. Assembly 170 may further comprise elongated openings 179, that serve the purpose of a slot, configured to optionally use a strap (not shown) to secure the leg. Importantly, driver rod 141 as shown here, may include discrete inhibitor features 145.

Figure 37:
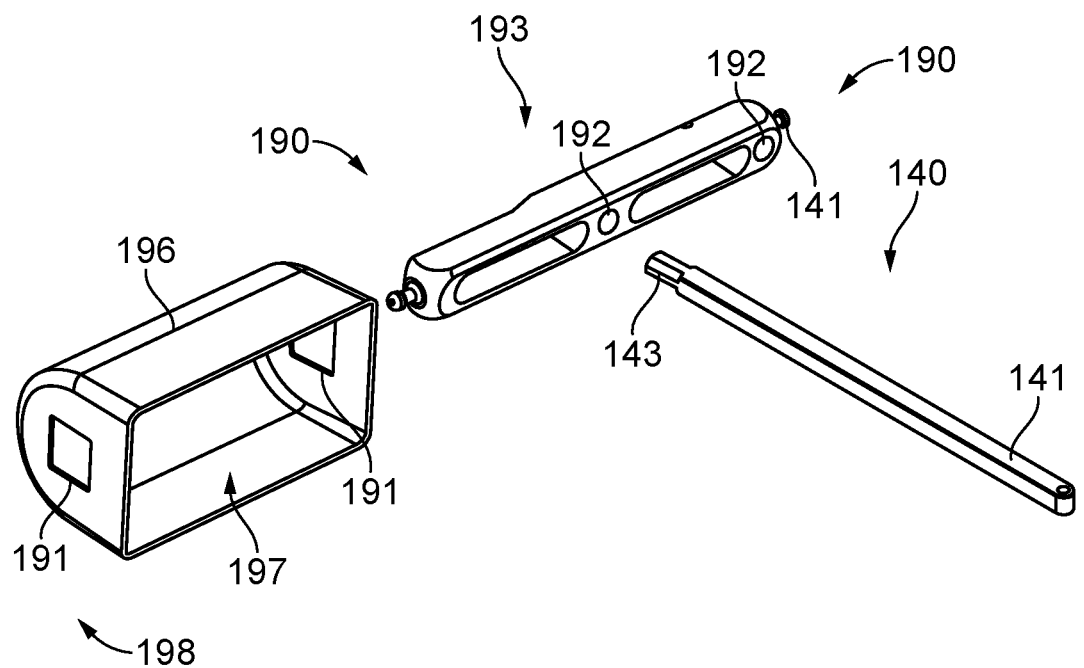
FIG. 37 illustrates an exploded perspective view of an injection-molded position pad assembly thereof.
Figure 38:
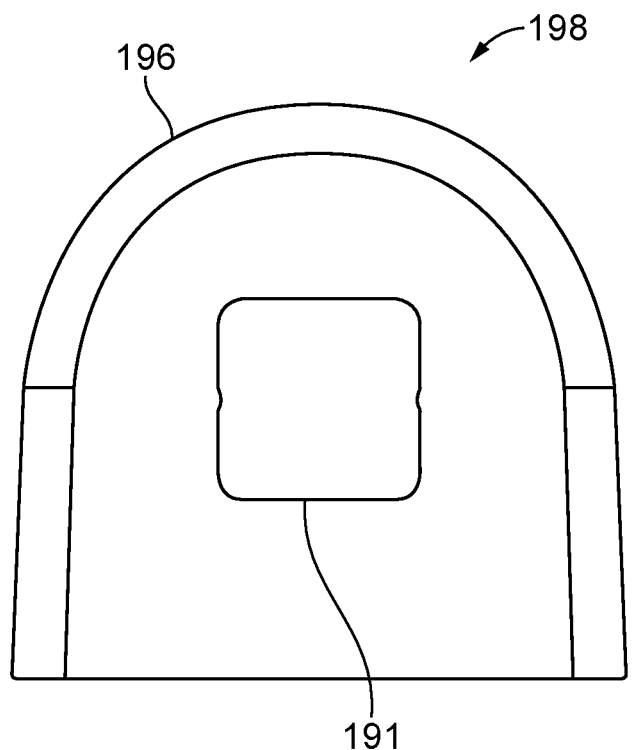
FIG. 38 illustrates a side view of an injection-molded position pad assembly thereof.
Figure 39:
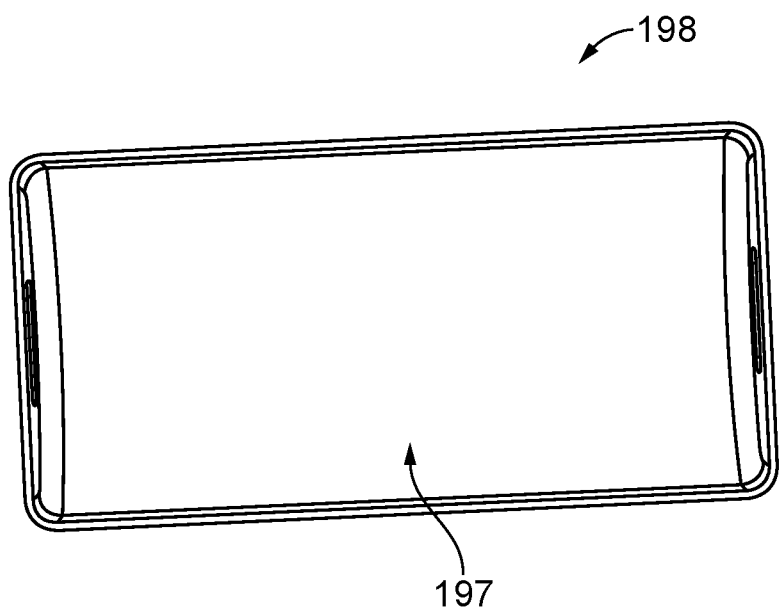
FIG. 39 illustrates a bottom view of an injection-molded position pad assembly thereof.
Figure 40:
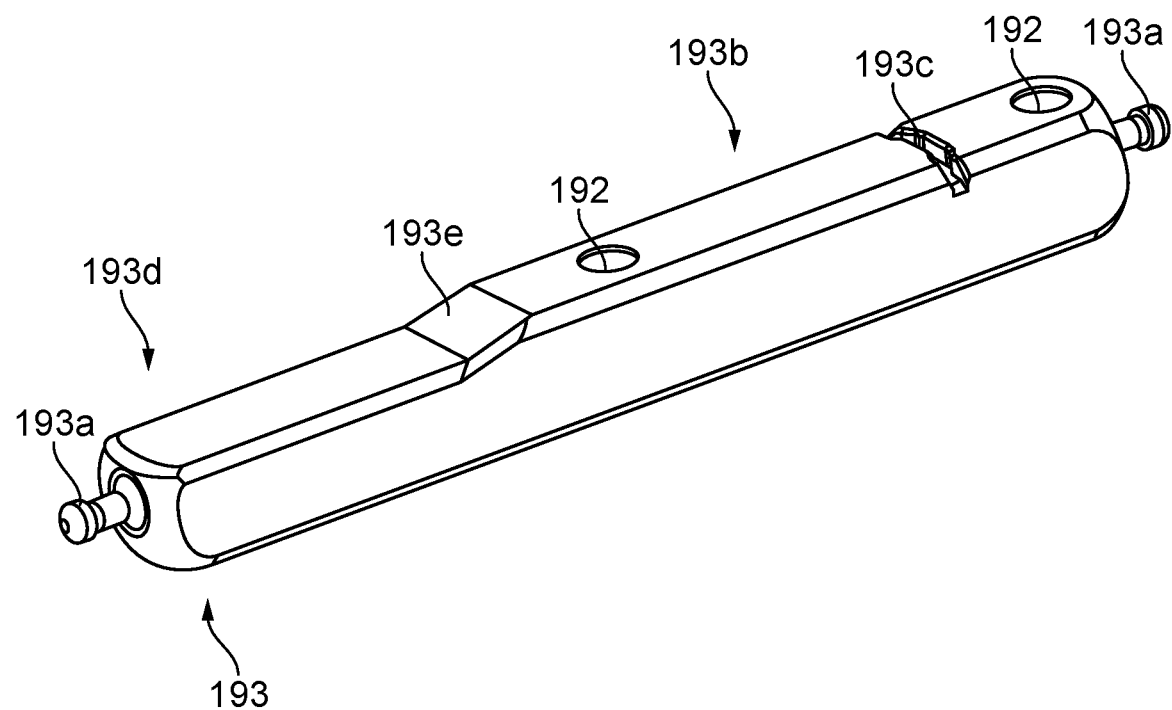
FIG. 40 illustrates a perspective view of a cross support in accordance with an embodiment of the present disclosure.
Figure 41:
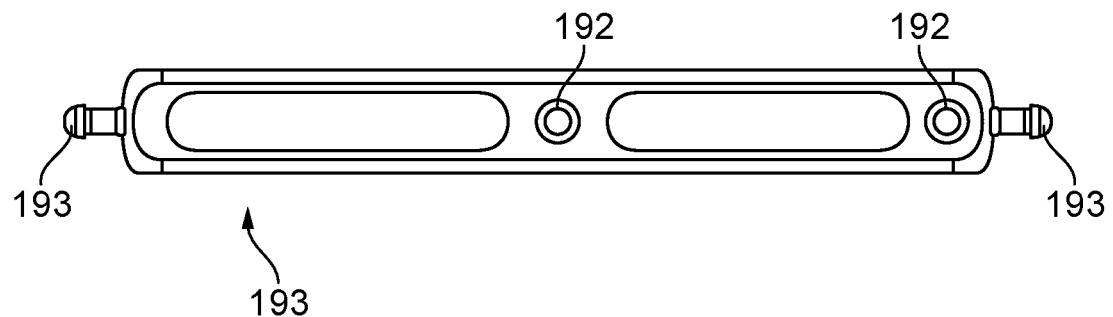
FIG. 41 illustrates a bottom view of a cross support thereof.

Referring now to FIGS. 36-41, an embodiment of driver rod assembly 140 and an alternative embodiment of an injection-molded positioner pad assembly 190 is provided. As shown in FIG. 37, driver assembly 140 may include driver rod 141 and driver support 143. Here, however, a positioner pad assembly 190 may include a shell 198 and a cross support 193. Shell 198 may include one or more positioner openings 191, an exterior surface 196 configured to hold a pad 194 (not shown) in a similar manner as other embodiments, and an interior cavity 197. Cross support 193 may comprise a first portion 193*b*, and second portion 193*d*, and a transition 193*e* disposed therebetween. Disposed at either end of cross support 193 may be disposed one or more support projections 193*a*, configured as an anchor point for retractors to hold the patient's skin open during surgery, thus advantageously freeing up the hands of a nurse or other surgical personnel. Along the first portion 193*b* may be disposed a support feature 193*c* and one or more support openings 192, the latter being configured to accept and couple to driver support 143. The first portion 193*b* may have a larger cross-sectional area than that of second portion 193*d*, and transition 193*e* may taper from one to the other accordingly. When coupled, the transition 193*e* may have no play relative to shell 198, and the different cross-sectional areas are configured for ease of insertion, holding, and may provide superior holding capability for a configuration where the driver rod 143 is secured at a support opening 192 disposed at an end. Support feature 193*c* may couple to the shell 198 by snap fitting into place around positioner opening 191.

Figure 42:
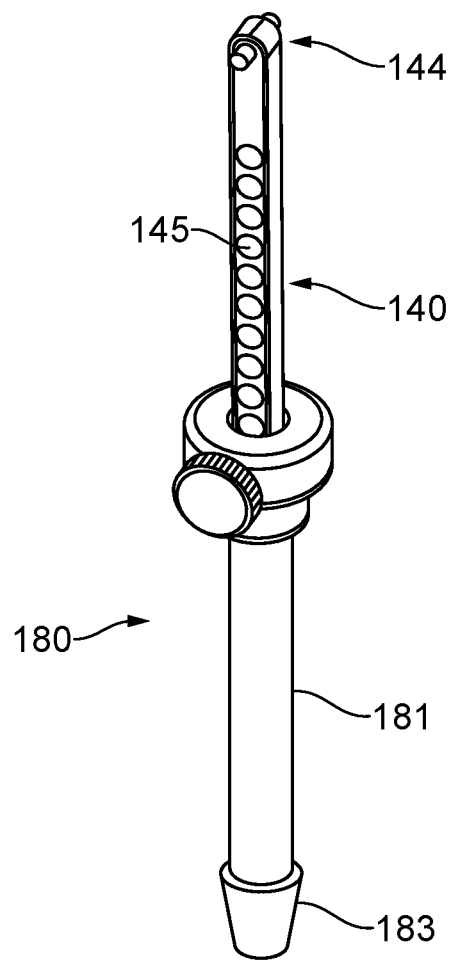
FIG. 42 illustrates a perspective view of a static adapter assembly in accordance with an embodiment of the present disclosure.
Figure 43:
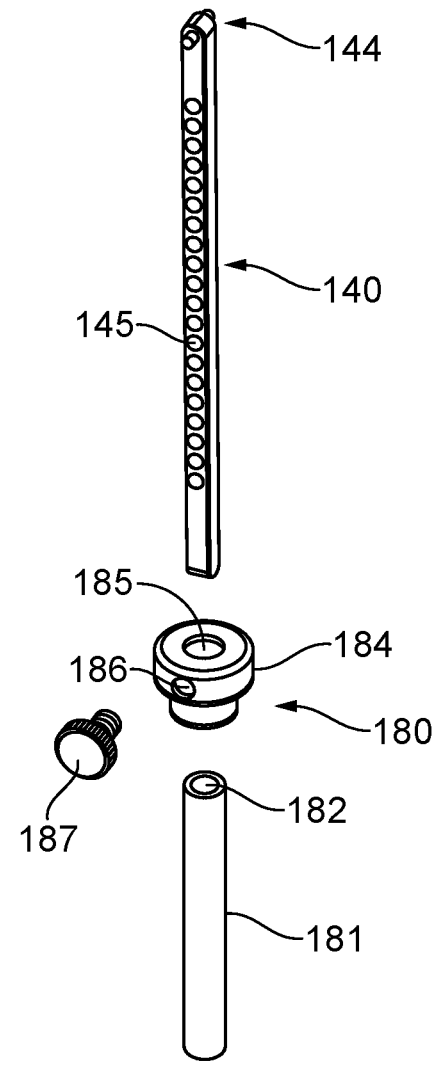
FIG. 43 illustrates an exploded perspective view of a static adapter assembly thereof.

Referring now to FIGS. 42 and 43, in an alternative embodiment, a static adapter portion 180 is shown. In combination with a driver assembly which may have discrete inhibitor features 145 located thereon, static adapter portion 180 provides a simplified alternative to the dynamic capabilities provided in a separate embodiment of modular distractor 100. Static adapter portion 180 may comprise a body 181 having a body opening 182 extending at least partial therethrough, and which may have a tapered end, configured to couple to a carriage assembly 105 having carriage openings 106*a* and/or 106*b*. Alternatively, static positioner 180 may be configured to couple directly to a side rail 102 of an operating table 101, or another other combination described herein. Static positioner 180 may further comprise a head 184 disposed at an end of body 181, head 184 having a head opening 185 extending therethrough, and a knurled knob opening 186 configured to accept a knurled knob 187, which may in turn be configured to provide holding and support of a driver rod 141 at the discrete inhibitor features 145.

The previous description of the disclosed embodiments is provided to enable any person skilled in the art to make or use the invention. Various modifications to these embodiments will be readily apparent to those skilled in the art, and the generic principles defined herein can be applied to other embodiments without departing from the spirit or scope of the invention. For example, any combination of the modular components comprising modular distractor 100 may be utilized, as well as others contemplated by, and within the scope of, this disclosure. Therefore, the present embodiments may be considered in all respects as illustrative and not restrictive.

What is claimed is:

1. A modular distractor system comprising:
   an adapter portion including a body having a first end, a second end a middle portion, and an opening extending from said first end through to at least a portion of said body, said adapter portion configured to couple to a side rail of an operating room table at said second end;
   a distractor housing comprising a distractor assembly comprising:
   a lower opening configured to receive said adapter portion at said first end;
   an extension bracket including an extension opening and being coupled to an extension spring, said extension bracket and spring being located at least partially within a first body cavity portion of said distractor housing;
   a release bracket including hold, curved and contact release portions, said hold portion having a release opening, said release bracket being coupled to a compression spring, said release bracket and compression spring being located at least partially within a second body cavity portion of said distractor housing; and
   a lever including contact, pivot, and driver portions, said lever being operably connect to said distractor housing at said pivot portion;
   a driver assembly comprising a driver rod and a driver support, said driver rod is configured to be received within said distractor housing along a length of said driver rod, said driver rod further configured to pass through said compression and extension springs and said extension and release openings, such that when said lever is moved along said contact portion, said lever pushes against said extension bracket to drive said support driver in a linear direction away from said distractor housing from a first position to a second position, and alternatively when said release bracket is depressed at said contact release portion, said driver support returns to said first position; and a patient positioner pad comprising a positioner body and a pad coupled thereto, the positioner body being configured to couple to said driver portion along at least a portion of said driver support so that when said driver support is moved, said patient positioner pad also moves.

* * * * *